United States Patent

Mott et al.

[11] Patent Number: 5,130,467
[45] Date of Patent: Jul. 14, 1992

[54] ACRYLATE ESTERS OF 1,1,1-TRISHYDROXYPHENYLETHANE

[75] Inventors: Graham N. Mott, Corpus Christi, Tex.; Thomas S. Johnson, Bridgewater, N.J.

[73] Assignee: Hoechst Celanese Corporation, Somerville, N.J.

[21] Appl. No.: 595,887

[22] Filed: Oct. 11, 1990

Related U.S. Application Data

[63] Continuation-in-part of Ser. No. 576,630, Aug. 31, 1990, abandoned.

[51] Int. Cl.⁵ .................... C07C 69/76; C07C 69/00
[52] U.S. Cl. ................................ 560/140; 560/104
[58] Field of Search ......................... 560/140, 104

[56] References Cited

U.S. PATENT DOCUMENTS

| | | |
|---|---|---|
| 3,544,514 | 5/1983 | Schnell et al. . |
| 3,579,542 | 4/1983 | Meyer et al. . |
| 4,394,496 | 6/1985 | Schrader . |
| 4,774,274 | 9/1988 | Takata et al. ............... 560/140 |
| 4,939,196 | 7/1990 | Sasaki et al. ............... 560/140 |

*Primary Examiner*—Paul J. Killos
*Attorney, Agent, or Firm*—Richard S. Roberts; Donald R. Cassady

[57] ABSTRACT

Compositions of matter, which are mono-, di- or tri-acrylate esters of 1,1,1-trishydroxyphenylethane and a method for the production of such esters by acrylating 1,1,1-tris(4'-hydroxyphenyl)ethane.

3 Claims, No Drawings

ACRYLATE ESTERS OF 1,1,1-TRISHYDROXYPHENYLETHANE

CROSS REFERENCE TO RELATED APPLICATION

This application is a continuation-in-part of U.S. Pat. application Ser. No. 07/576,630, filed Aug. 31, 1990, which is incorporated herein by reference.

BACKGROUND OF THE INVENTION

The present invention relates to acrylate esters of 1,1,1-trishydroxyphenylethane (THPE) or more particularly to mono-, di-, and triacrylated esters of THPE. The invention also relates to a process for their preparation, their use as multifunctional polymerizable monomers, and homo- and co-polymers produced therefrom. Such compounds find use in the production of protective coating compositions, adhesives, photosensitive compositions, and the like.

Acrylate esters of 1,1,1-trishydroxyphenylethane may be produced by reacting 1,1,1-tris(4'-hydroxyphenyl)ethane with an acrylating agent as hereinafter described. It is known in the art that the intermediate 1,1,1-tris(4'-hydroxyphenyl)ethane may be produced by reacting 4-hydroxyacetophenone with phenol. Typically this is performed with phenol also used as the solvent for the mixture. THPE itself may be produced according to a method described in U.S. Pat. application No. 07/478,072, filed Feb. 9, 1990, now U.S. Pat. No. 4,992,598 which is incorporated herein by reference. According to that disclosure, very pure THPE is obtained by washing a crude reaction mixture of 4-hydroxyacetophenone and phenol with a THPE saturated wash/methanol liquid prior to a recrystallization. It has been found that by use of such a wash yields of pure white THPE are good, and solvents have a more productive use. As a result of the process, most of the color bodies are removed in the wash stage where the color of the crude THPE changes from a dark rusty color to a light tan. The balance is removed in the recrystallization. With crude THPE washed with recycled recrystallization filtrate, only a single recrystallization from methanol/water is necessary to meet white color and high purity requirements. This recrystallization is basically a precipitation of THPE from the methanol/water solution. By acrylating THPE, one produces the inventive monomeric mono-, di-or tri-acrylate esters of 1,1,1-trishydroxyphenylethane. These may be polymerized, copolymerized and/or crosslinked by the use of known free radical polymerization and crosslinking techniques.

SUMMARY OF THE INVENTION

The invention provides, as a composition of matter, mono-, di- and tri-acrylate esters of 1,1,1-trishydroxyphenylethane. The invention also provides a method for the production of acrylate esters of 1,1,1-trishydroxyphenylethane which comprises acrylating 1,1,1-tris(4'-hydroxyphenyl)ethane. The inventive compounds have the general formula

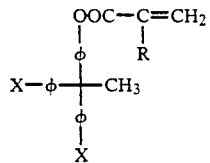

where $\phi$ = a phenylene group $$X = -OH \text{ or } -OOC-\underset{R}{C}=CH_2, \text{ and}$$

R=H, alkyl or aryl, preferably $C_1$–$C_6$ alkyl or $C_6$–$C_{10}$ aryl.

The invention also comprises homopolymers and copolymers of these monomers as well as a method for preparing such homopolymers and copolymers by free radical initiating the monomers. Articles may be prepared by disposing such compositions on substrates such as metals, plastics, and the like.

DETAILED DESCRIPTION OF THE PREFERRED EMBODIMENT

As hereinbefore mentioned, the production of 1,1,1-tris(4'-hydroxyphenyl)ethane may be performed by the reaction of 4-hydroxyacetophenone with phenol, wherein phenol is the supporting solvent as well as a reagent. The reaction takes place under catalytic conditions, with hydrochloric acid and beta-mercaptopropionic acid as preferred co-catalyst. The resulting reaction product contains significant amounts of impurities which are removed as described hereinafter. An impure, substantially solid crude admixture of freshly produced THPE contains 1,1,1-tris(4'-hydroxyphenyl)ethane (THPE), residual 4-hydroxyacetophenone, phenol, chlorides, THPE isomers, bis-(hydroxyphenyl)ethene isomers, color bodies and other unidentified parts which are sought to be removed. 1,1,1-Tris(4'-hydroxyphenyl)ethane may be obtained from a substantially solid crude admixture containing 1,1,1-tris(4'-hydroxyphenyl)ethane and the impurities resulting from the catalytic production of 1,1,1-tris(4'-hydroxyphenyl)ethane from 4-hydroxyacetophenone and phenol. The THPE purification method proceeds by:

a) washing the crude admixture with a saturated solution of 1,1,1-tris(4'-hydroxyphenyl)ethane in a solute comprising from about 60% to about 75% by weight of water and from about 25% to about 40% by weight of methanol; and b) isolating the washed crude admixture from the formed effluent washing composition, and dissolving the washed crude admixture in methanol, and c) adding sufficient water and sodium borohydride to the dissolved, washed crude admixture to form a precipitate of 1,1,1-tris(4'-hydroxyphenyl)ethane, and d) filtering the precipitate to thereby form a purified 1,1,1-tris(4'-hydroxyphenyl)ethane and a filtrate; and e) rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from the precipitate.

In the first step of the purification method, one washes the crude admixture with a saturated solution of 1,1,1-tris(4'-hydroxyphenyl)ethane in a solute comprising from about 60% to about 75% by weight of water and from about 25% to about 40% by weight of methanol. Preferably this washing is conducted in several washing steps. It has been found that by employing a saturated solution of THPE in the washing solution, that THPE loss from the crude admixture is substantially reduced. Prior to washing, the crude admixture typically contains from about 15% to about 30% by weight of residual phenol. Since phenol is a good solvent for THPE, it is desired to reduce the phenol content prior to the washing step simply by vacuum draw of the phenol.

However, it has been found that if too much phenol is drawn off, that although the THPE recovery is good, the purity of the product is unsatisfactory. Loss of THPE during the wash of the crude admixture is basically caused by the presence of phenol although the washing solution is THPE saturated. Phenol content may be controlled by pumping off the crude admixture before the wash or by use of a hot nitrogen flow through the crude admixture to cause the phenol, which is the most volatile component, to leave the system before the wash. Generally it is desired to obtain THPE with 99.5% or greater purity and having a whiteness measure (APHA) of 200 or less, preferably 150 or less. Therefore phenol content of at least about 1.0% and up to about 30.0% based on the weight of the crude admixture is desired. More preferably the phenol content is adjusted to from about 4.0% to about 10% and most preferably from about 4.5% to about 7.5%. A single most preferred phenol content is about 5.0%. Therefore, in the most preferred case, the phenol content of the crude admixture is first adjusted to these levels before conducting the washing step.

Next, after the washing step, one isolates the washed crude admixture from the formed effluent washing composition. This can be done by performing the washing on a filter plate while stirring and then drawing down the filtrate. The solid, washed crude admixture is then dissolved in sufficient methanol to effect a dissolution.

One then adds sufficient water and sodium borohydride to reduce the dissolved, washed crude admixture and to form a precipitate of 1,1,1-tris(4'-hydroxyphenyl)ethane. The sodium borohydride also acts as a pH adjusting reagent during the recrystallization. In the preferred embodiment, the amount of sodium borohydride added ranges from about 0.0003% to about 0.3%, preferably from about 0.003% to about 0.07% and most preferably from about 0.01% to about 0.03% based on the weight of methanol and water. If the phenol content in the crude admixture has been reduced prior to washing, it is preferred that sodium borohydride is added to the methanolic solution THPE solution. After stirring, the carbon in the form of charcoal, is added to the methanolic THPE solution and filtered off prior to having added more sodium borohydride plus water. This is most advantageous when the phenol content has been reduced to 15% or less in the pre-washed crude admixture. In the preferred embodiment, the amount of carbon added ranges from about 0.001% to about 1.0%, preferably from about 0.01% to about 0.8%, and most preferably from about 0.05% to about 0.3% based on the weight of methanol.

One then filters the precipitate to thereby form a purified, recrystallized 1,1,1-tris(4'-hydroxyphenyl)ethane nd a filtrate. The next step is rinsing the resultant filtered precipitate of 1,1,1-tris(4'-hydroxyphenyl)ethane with a solution of sufficient methanol and water, which optionally contains 1,1,1-tris(4'-hydroxyphenyl)ethane up to the saturation point, and conducting the rinsing for a sufficient time to remove substantially all residual colored impurities from said precipitate. The rinse mixture preferably comprises water and methanol in a 2:1 to 6:1 weight ratio. One may perform an optional stabilizing rinse with an aqueous sodium dithionate solution at this stage. Typical sodium dithionate solutions may range from about 0.01% to about 1.0%, preferably from about 0.05% to about 0.5% by weight in water. Finally, the product is dried.

It has been found that one may use this colored, resultant filtrate as the washing solution in the washing step of another crude admixture batch. Although this filtrate contains sodium borohydride and removed, colored bodies and other impurities in addition to water, methanol and THPE, it has been found that these are substantially removed in the effluent of the washing step. If the filtrate color is pink one should treat it with sodium dithionate to change it to a light yellow color prior to using the filtrate to wash the next batch of crude admixture. A suitable amount is about 0.1 weight percent of saturated aqueous sodium dithionate. Therefore, this filtrate serves double duty in the overall process and significantly reduces the amount of fluids which must be recycled or treated before ultimate discharge.

The acrylate esters of 1,1,1-trishydroxyphenylethane may be produced by reacting the 1,1,1-tris(4'-hydroxyphenyl)ethane with an acrylating agent under suitable reaction conditions. The degree of esterification may be controlled by regulating the amount of the acrylating agent used. The most preferred acrylating agent is acryloyl chloride.

The monomer may be polymerized by a free radical initiation process to produce homopolymers such that it has a molecular weight in the range of from about 200,000 to about 10,000,000 preferably from 200,000 to about 1,000,000 or more preferably about 500,000 to about 1,000,000. It is predicted that essentially any free radical initiation system will serve for this purpose. One free radical initiation method is by photopolymerization wherein the acrylated THPE is admixed with a photopolymerization initiator in a suitable solvent composition and thereafter exposed to light. One preferred free radical initiator is azoisobutyronitrile. Other azo type initiators are also suitable. Still others non-exclusively include peroxides such as benzoyl peroxide, and di-t-butyl peroxide. Free radical liberating photoinitiators include any compound which liberate free radicals on stimulation by actinic radiation. Preferred photoinitiators nonexclusively include quinoxaline compounds as described in U.S. Pat. No. 3,765,898; the vicinal polyketaldonyl compounds in U.S. Pat. No. 2,367,660; the alpha-carbonyls in U.S. Pat. Nos. 2,367,661 and 2,367,670; the acyloin ethers in U. S. Pat. No. 2,448,828; the triarylimidazolyl dimers in U.S. Pat. No. 3,479,185; the alpha-hydrocarbon substituted aromatic acyloins in U.S. Pat. No. 2,722,512; polynuclear quinones in U.S. Pat. Nos. 2,951,758 and 3,046,127; and s-triazines in U.S. Pat. No. 4,656,272. All of the foregoing patents are incorporated herein by reference. In the practice of the present invention, the photoinitiator component is preferably blended with the acrylated THPE, in a suitable solvent composition, an amount ranging from approximately 2% to 30% based on the weight of the solids in the mixture. A more preferred range is from approximately 6% to 20%.

The polymer set forth above is preferably a homopolymer, but it may also be a copolymer wherein the co-monomers are units of styrene, acrylates, methacrylates and maleimides. The co-monomer unit may optionally be substituted with a variety of pendant groups in order to adjust the properties of the compound as desired by the user. Specifically, the aforementioned acrylated THPE monomer may be co- or terpolymerized under the foregoing polymerization conditions in the presence of one or more additional monomers which may be ethylenically unsaturated compounds, acetoxystyrene, substituted acetoxystyrene, hydroxystyrene, substituted hydroxystyrene, maleic anhydride, maleimides, styrene, acrylates and methacrylates such as methyl methacrylate, and butyl acrylate wherein the copolymer or terpolymer has an average molecular weight in the range given above.

Preferably the acrylated THPE monomer is co-polymerized with a compound which is an addition polymerizable, nongaseous (boiling temperature above 100° C. at normal atmospheric pressure), ethylenically unsaturated compound containing at least two terminal ethylenically unsaturated groups, which is capable of forming a high molecular weight polymer by free radical initiated, chain propagating addition polymerization. Suitable polymerizable materials nonexclusively include triethylene glycol dimethacrylate, tripropylene glycol diacrylate, tetraethylene glycol dimethacrylate, diethylene glycol dimethacrylate, 1,4-butanediol diacrylate, 1,6-hexanediol dimethacrylate, pentaerythritol tetraacrylate, trimethylol propane triacrylate, trimethylol propane trimethacrylate, di-pentaerythritol monohydroxypentaacrylate, pentaerythritol triacrylate, bisphenol A ethoxylate dimethacrylate, trimethylolpropane ethoxylate triacrylate, and trimethylolpropane propoxylate triacrylate.

One may employ the foregoing homopolymers, copolymers and terpolymers in protective surface coatings and adhesive blends. They may also be used in admixture with a photosensitizing agent to form a photographic element such as a photoresist. In the production of a photosensitive composition and photographic element, one blends the above produced polymer with a photosensitizer and a suitable solvent until a homogeneous solution is formed. The solution is then coated on a suitable substrate and dried until it is non-tacky. It is then imagewise exposed to light and developed. Photosensitizers are known to the skilled artisan as demonstrated by Light Sensitive Systems, Kosar, J.; John Wiley & Sons, New York, 1965 which is incorporated herein by reference. The monomer may also be used as a component of a photopolymerizable element wherein the monomer, initiator and a solvent are coated on a support, dried, and imagewise exposed to light with subsequent development. In another embodiment, the acrylated polymer may be crosslinked by admixture with a crosslinking agent with subsequent heating. In one case the acrylated THPE polymer and crosslinking agent are mixed, coated on a support, and crosslinked with heat in the presence of a catalytic amount of an acid.

The crosslinking component is a compound, which when in the presence of heat, and preferably a catalytic amount of acid, is capable of crosslinking the foregoing acrylated THPE polymer. Crosslinking compounds for such use have the general formula

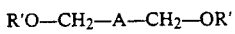

R'O—CH$_2$—A—CH$_2$—OR' wherein A is a monomeric, aromatic hydrocarbon having one or more fused or unfused, separated or unseparated rings and each R unit is independently H, (C$_1$–C$_6$) alkyl, (C$_3$–C$_6$) cycloalkyl, aryl or arylalkyl.

The preferred crosslinking compound is dimethylol paracresol as described in U.S. Pat. No. 4,404,272 which is incorporated by reference, and its ether and ester derivatives including phenol, 2,6-bis(hydroxyethyl)-4-methyl; benzene, 1-methoxy-2,6-bis-(hydroxymethyl-4-methyl; phenol, 2,6-bis(methoxymethyl)-4-methyl; and benzene, 1-methoxy-2,6-bis(methoxymethyl)-4-methyl; methyl methoxy diphenyl ether, melamine formaldehyde resins and compounds and alkylated analogous thereof having 1 to about 3 monomer units such as those typically sold under the trade names Cymel from American Cyanamid and Resimene from the Monsanto Company, for example hexamethylol melamine hexamethyl ether.

In the preferred photoresist composition, the crosslinking compound is present in a mixture with the acrylated THPE monomer, polymer or copolymer in an amount of from about 0.5 to about 7 weight percent of the solid components of the composition, more preferably from about 2 to about 6 weight percent, and most preferably from about 3 to about 5 weight percent.

The following non-limiting examples serve to illustrate the invention.

EXAMPLE 1

1,1,1-tris(4'-acryloxyphenyl)ethane 318 g (1.04 mol) 1,1,1-Trishydroxyphenylethane, 314 g (3.08 mol) triethylamine, 0.75 g methylhydroquinone and 500 ml of methylene chloride are added to a 5 liter flask and cooled to 0° C. A mixture of 300 g (3.3 mol) of acryloyl chloride, and 1300 ml of methylene chloride are added over a four hour period while maintaining the temperature at 0° C. When the mixing is complete, the mixture is allowed to warm to room temperature and stirred overnight. Several liters of water are added to precipitate triethylammonium hydrochloride. The organic phase is separated and dried over magnesium sulfate. After adding an additional 0.25 grams of methylhydroquinone, the organic phase is evaporated using an air sparge, affording a light yellow viscous liquid.

EXAMPLE 2

1,1,1-tris(4'-acryloxyphenyl)ethane 30.6 g (0.1 mol) of 1,1,1-trishydroxyphenylethane, 30.3 g (0.3 mol) of triethylamine, 0.25 grams of methylhydroquinone and 150 ml of tetrahydrofuran are added to a flask at 0° C. A mixture of 27.5 g (0.3 mol) of acryloyl chloride and 50 ml of tetrahydrofuran are added over three hours and left to stir overnight. 200–300 ml of water are added. The tetrahydrofuran solution is precipitated, evaporated and dried to yield 48–49 grams of a thick, light yellow liquid.

EXAMPLE 3

111.3 grams of 1,1,1-trishydroxyphenylethane, 110.2 grams of triethylamine, 0.25 grams of methylhydroquinone and 200 ml of methylene chloride are added to a flask at 0° C. Then 100 grams of acryloyl chloride, and 500 ml of methylene chloride are added over four hours to yield a light yellow solution with a heavy precipitate. Two liters of water are added. The methylene chloride is extracted and the mixture is dried. 0.25 grams of methylhydroquinone are added and the mixture is evaporated under an oxygen sparge.

What is claimed is:

1. Mono-, di- and tri- acrylate esters of 1,1,1-trishydroxyphenylethane having the formula

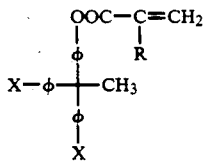

where $\phi$ = a phenylene group $$X = -OH \text{ or } -OOC-\underset{R}{C}=CH_2, \text{ and}$$

R = H, alkyl or aryl.

2. The acrylated esters of claim 1 wherein R is $C_1$-$C_6$ alkyl or $C_6$-$C_{10}$ aryl.

3. The acrylated esters of claim 1 wherein each X is

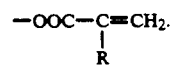

* * * * *